United States Patent [19]
Atkinson et al.

[11] Patent Number: 5,992,462
[45] Date of Patent: Nov. 30, 1999

[54] DISC TYPE CHECK VALVE

[75] Inventors: Gordon E. Atkinson, Cedarville; James C. Bailey, Yellow Springs, both of Ohio

[73] Assignee: Vernay Laboratories, Inc., Yellow Springs, Ohio

[21] Appl. No.: 09/182,575

[22] Filed: Oct. 28, 1998

[51] Int. Cl.$^6$ .............................. F16K 15/14; F16K 15/00
[52] U.S. Cl. ........................ 137/854; 137/852; 137/515.5
[58] Field of Search ...................... 137/854, 852, 137/515.5; 604/247

[56] References Cited

U.S. PATENT DOCUMENTS

| | | |
|---|---|---|
| 274,308 | 3/1883 | George . |
| 2,051,023 | 8/1936 | Bullard ..................... 128/140 |
| 2,526,346 | 10/1950 | Goldinger ............... 137/515.5 |
| 2,722,370 | 11/1955 | Owsen et al. ................... 230/2 |
| 3,194,263 | 7/1965 | Riester ....................... 137/508 |
| 3,623,504 | 11/1971 | Davis ........................ 137/852 |
| 3,827,456 | 8/1974 | Sheppard .................. 137/525 |
| 3,983,857 | 10/1976 | O'Connor ............. 123/185.5 R |
| 3,990,439 | 11/1976 | Klinger .................... 128/142.4 |
| 4,355,653 | 10/1982 | Credle, Jr. .................. 137/102 |
| 4,416,445 | 11/1983 | Coad ............................ 267/35 |
| 4,514,742 | 4/1985 | Suga et al. ............... 346/140 R |
| 4,556,086 | 12/1985 | Raines ....................... 137/852 |
| 4,677,447 | 6/1987 | Nielsen ................... 346/140 R |
| 4,683,916 | 8/1987 | Raines ....................... 137/854 |
| 4,711,224 | 12/1987 | Eckhardt .................... 123/572 |
| 4,712,583 | 12/1987 | Plemulder et al. ........ 137/852 |
| 4,749,003 | 6/1988 | Leason ...................... 137/854 |
| 4,762,149 | 8/1988 | Pickl, Jr. .................... 137/854 |
| 4,805,661 | 2/1989 | Knapp et al. .............. 137/218 |
| 4,827,973 | 5/1989 | Boehmer ................... 137/854 |
| 4,898,581 | 2/1990 | Iwatschenko ............. 137/854 |
| 4,946,448 | 8/1990 | Richmond ................. 604/247 |
| 4,986,310 | 1/1991 | Bailey et al. .............. 137/859 |
| 5,203,872 | 4/1993 | Naffziger ..................... 251/82 |
| 5,381,563 | 1/1995 | Isabelle et al. ............. 4/541.5 |

Primary Examiner—Denise L. Ferensic
Assistant Examiner—Joanne Y. Kim
Attorney, Agent, or Firm—Biebel & French

[57] ABSTRACT

A check valve including a housing formed by a base portion and a cap portion positioned in telescoping relation with each other. A disc shaped valve member is positioned within the housing and is defined by opposing first and second planar sides. The valve member includes a spherical portion located centrally thereon and which is captured between first and second valve supports supported on the base portion and cap portion, respectively. The valve supports hold the valve member in engagement with a valve seat, and the valve member moves out of engagement with the valve seat in response to a fluid pressure applied at a fluid inlet in the base portion to permit forward fluid flow while preventing fluid flow in the reverse direction.

14 Claims, 5 Drawing Sheets

DISC TYPE CHECK VALVE

BACKGROUND OF THE INVENTION

1. Field of the Invention

This invention relates generally to a flow regulation apparatus and, more particularly, to a check valve which will open at very low pressures to permit fluid flow in a first direction and which will close to prevent flow in a second direction with extremely low back flow leakage while withstanding high back pressures, and which is not sensitive to the position or orientation of the valve.

2. Description of the Prior Art

One requirement of one way flow or check valves, such as the type used in medical fluid flow lines, is that the valves offer little resistance to fluid flow in one direction and stop fluid flow in the opposite direction with low back flow leakage. A valve which is commonly used for this purpose is a duckbill valve which comprises a pair of valve lips which readily open at low forward flow pressures and which readily close to prevent back flow in an opposite direction. While this type of valve provides an effective mechanism for controlling fluid flow, they typically cannot withstand high back pressure if they are designed for low opening and forward pressure. Also, the assembly of duckbill valves into a housing typically requires care to ensure that the valve is properly oriented and aligned relative to the ends and sides of the housing in order ensure effective operation.

Another form of known check valve uses a disc shaped regulator element which is generally required to be centered within a housing. Reliable operation of the regulator element in such valves is sensitive to the precise centering of the regulator element within the valve housing and, in addition to requiring care in properly placing the regulator element in the valve housing during assembly, prior art regulators have been subject to misalignment by slipping off center during use, leading to unacceptable leakages of the valve. In addition, some disc valve designs are position sensitive and consequently also subject to failure or leakage.

While known check valves of the above described type and other check valve designs provide satisfactory operation for many applications, there is a continuing need for a check valve which reliably responds to permit fluid flow at low pressures, as well as preventing back flow with extremely low leakage of fluid, and which is of a simplified construction permitting ease of assembly, including automated assembly of the valve structure.

SUMMARY OF THE INVENTION

The present invention is a valve assembly which has a low opening pressure to allow fluid flow in a first direction and which is capable of withstanding high back pressures in preventing fluid flow in a second opposite direction.

The valve assembly comprises a housing formed of first and second portions which are joined together for enclosing a valve member. The first portion defines a fluid inlet and includes a first inner circumferential wall forming an upstream chamber adjacent to the fluid inlet. An inlet portion flange extends radially outwardly from the upstream chamber and defines a valve seat including a stepped portion engaging the valve member.

The valve member comprises a disc shaped element with substantially planar first and second sides. The first and second sides are symmetrical with respect to each other and each side includes a rounded protrusion located centrally of the valve member. The protrusions define an enlarged central portion for mounting the valve member.

First and second valve supports are supported on the first and second portions, respectively, for engaging the enlarged central portion of the valve member. Each of the first and second valve supports includes a rounded recess which corresponds to the curvature of the rounded protrusions. The valve assembly is conveniently assembled by placing the valve member within the first portion and subsequently engaging the second portion on the first portion. The cooperating rounded protrusions and recesses securely engage the valve member to hold it in position while permitting the valve member to assume an accurate orientation relative to the valve seat as the first and second portions are assembled together.

Therefore, it is an object of the present invention to provide a disc type check valve which opens at low pressures and which provides extremely low back flow leakage.

It is another object of the invention to provide such a check valve which is capable of withstanding high back pressures.

It is yet another object of the invention to provide a reliable and easily assembled check valve which meets the above criteria.

Other objects and advantages of the invention will be apparent from the following description, the accompanying drawings and the appended claims.

DETAILED DESCRIPTION OF THE PREFERRED EMBODIMENT

Figure 1:
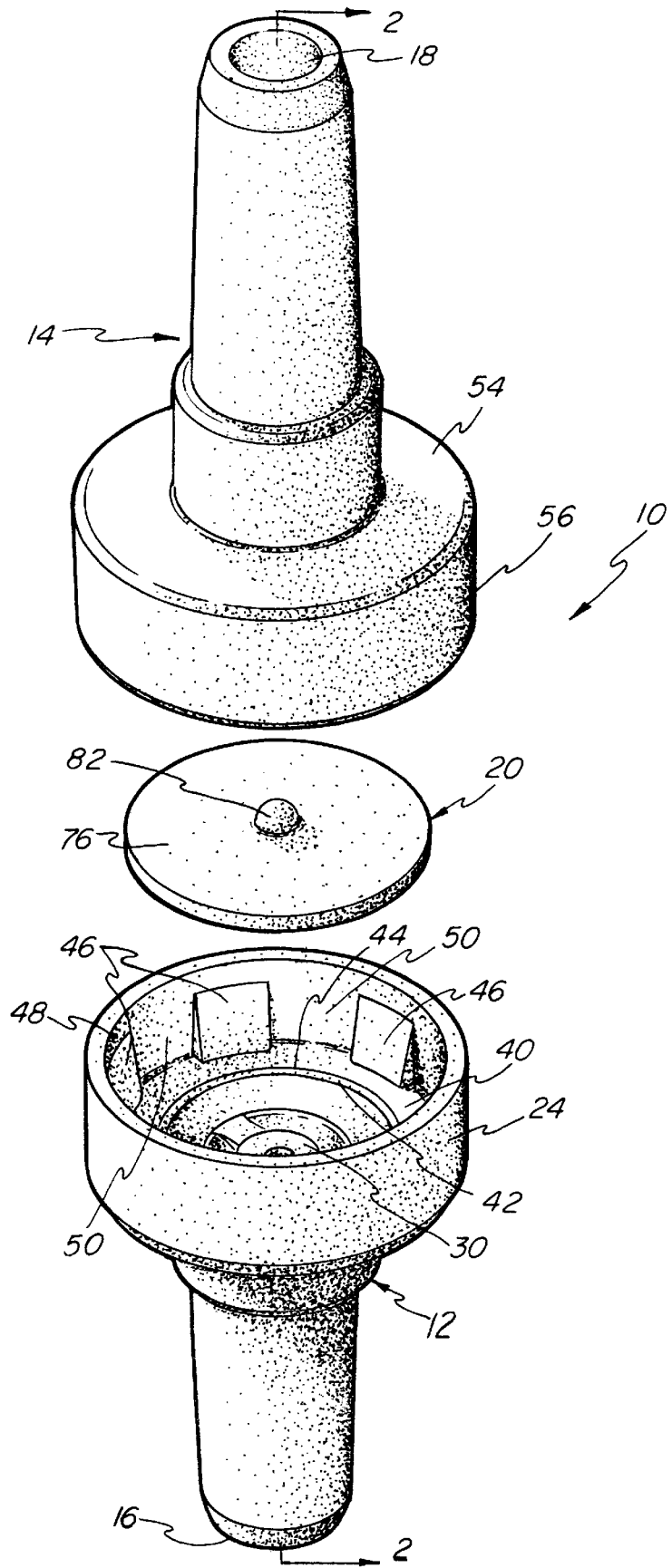
FIG. 1 is a perspective exploded view of a preferred embodiment of the check valve of the present invention.

Referring to the drawing figures, the check valve 10 of the present invention includes a housing defined by a first or base portion 12 and a second or cap portion 14 which is adapted to fit in telescoping relationship with the base portion 12. The base portion 12 includes a tubular end 16 defining a fluid inlet, and the cap portion 14 includes a tubular end 18 defining a fluid outlet for the valve 10. In addition, an elastomeric disc shaped valve member 20 is positioned within the housing between the base portion 12 and cap portion 14 for controlling fluid flow through the inlet 16 and outlet 18.

As may be best seen in FIGS. 2, 3, 5 and 6, the inlet 16 of the base portion 12 is defined by an annular wall 20. An inlet portion flange 22 extends radially outwardly from the wall 20, and a first annular lip 24 extends axially from an outer edge of the inlet portion flange 22. The lip 24 is provided for cooperating with the cap portion 14 and for facilitating alignment of the valve member 20, as will be described further below.

The base portion 12 further includes an upstream chamber 26 defined by a first inner circumferential wall 28. The chamber 26 is located adjacent the fluid inlet 16 and defines a cross sectional area greater than the cross sectional area of the fluid inlet 16. A first valve support 30 is supported within the chamber 26 by a pair of first rib members 32, 34 which extend radially inwardly from the inner wall 28 to hold the first valve support 30 in spaced relation to the inner wall 28. The first valve support 30 includes a surface 36 facing away from the inlet 16 and defining a rounded or circular recess 38 therein for engaging the valve member 20 in a manner to be described hereinafter.

The inlet portion flange 22 defines a valve seat 40 including a stepped portion 42 located radially intermediate the upstream chamber 26 and the first annular lip 24. The step portion 42 includes a radiused valve engaging edge 44 for engaging the valve member 20 in sealing engagement.

The base portion 12 further includes a plurality of circumferentially spaced guide tabs 46 located on the inner surface 48 of the inlet portion flange 24 whereby a plurality of slot areas 50 are defined between the tabs 46. The tabs 46 angle radially outwardly in a direction extending away from the inlet 16 and facilitate positioning of the valve member 20 during assembly of the check valve 10. The slots 50 located between the tabs 46 provide for increased fluid flow area when the check valve 10 is in an open forward flow condition.

Figure 2:
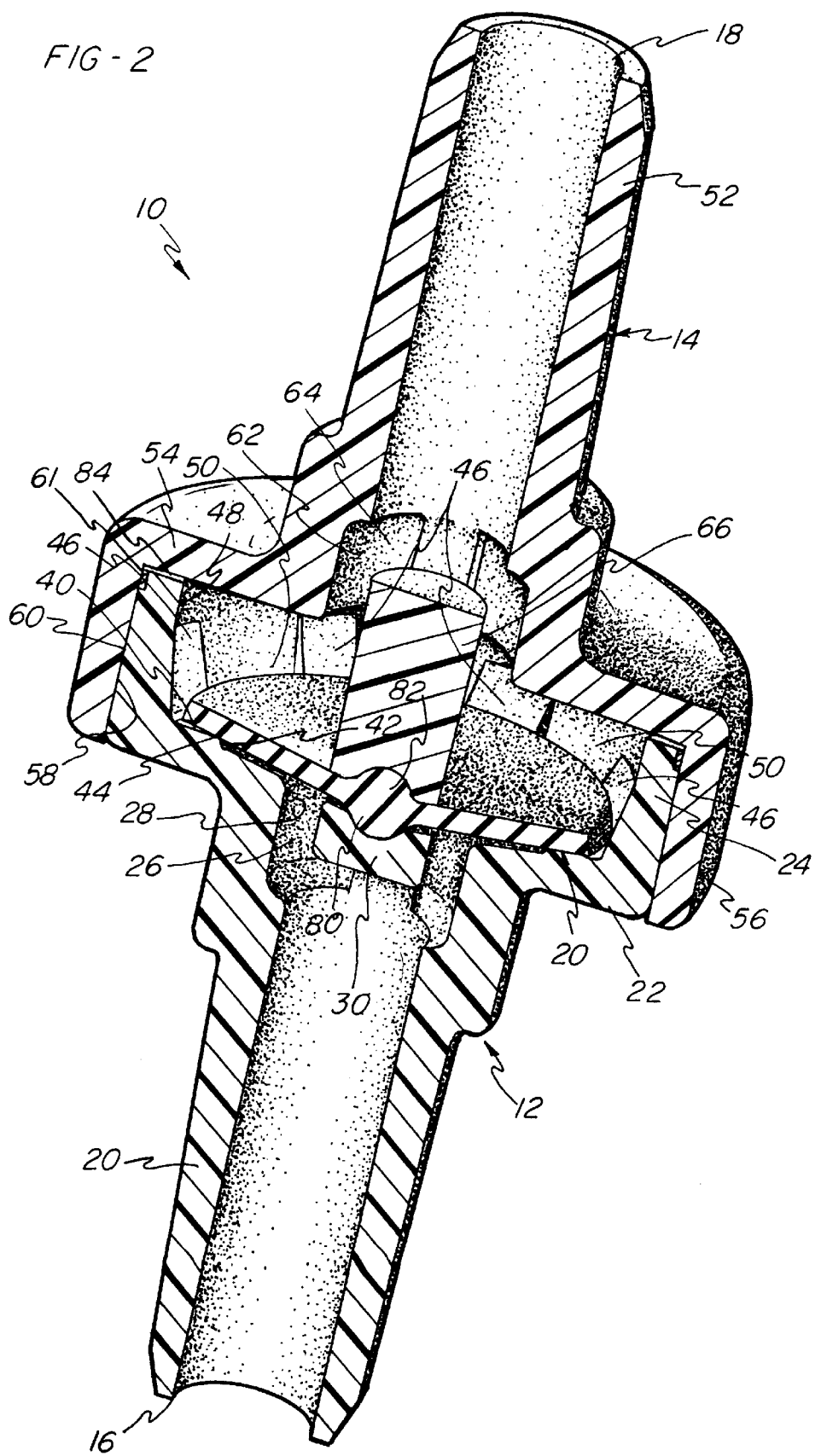
FIG. 2 is a perspective view of a cross section along line 2—2 in FIG. 1.
Figure 3:
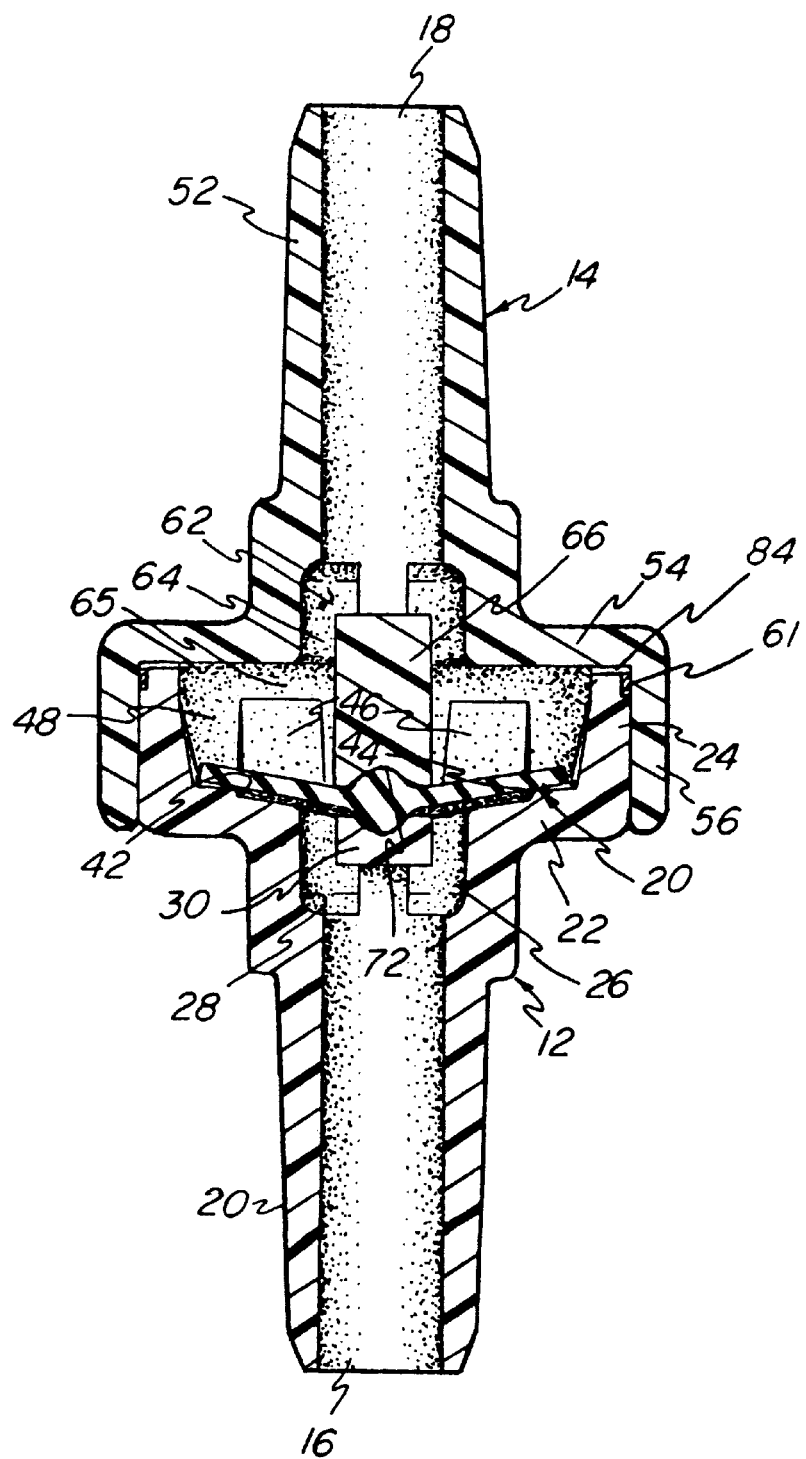
FIG. 3 is an elevational view of a cross section similar to FIG. 2.
Figure 4:
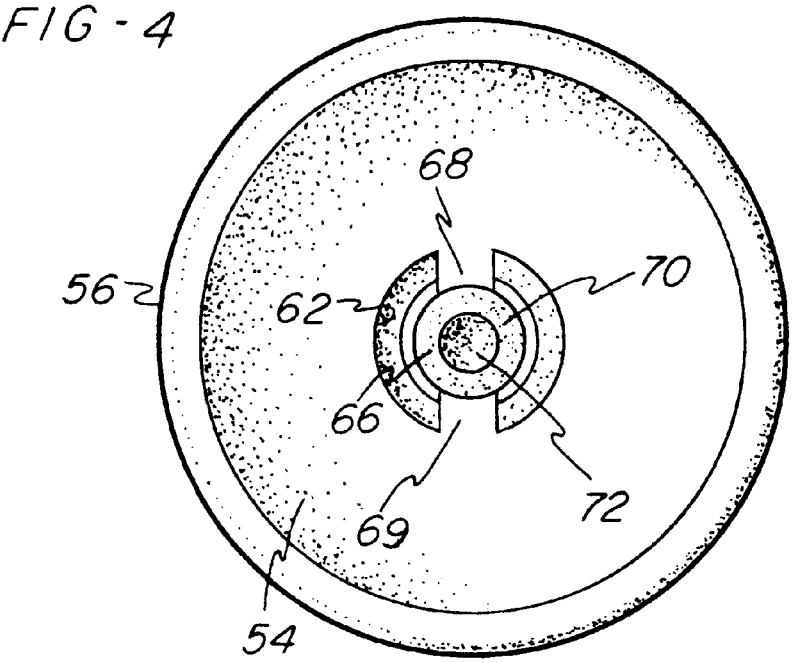
FIG. 4 is an end view of the inside of the cap portion for the valve.
Figure 7:
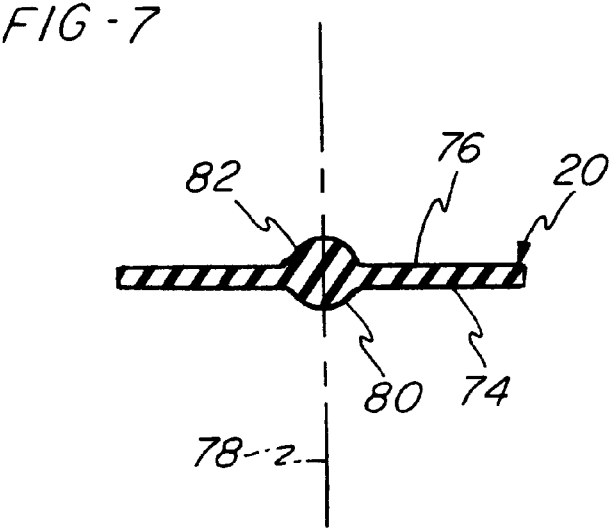
FIG. 7 is an elevational view of a cross section through the center of the valve member.
Figure 5:
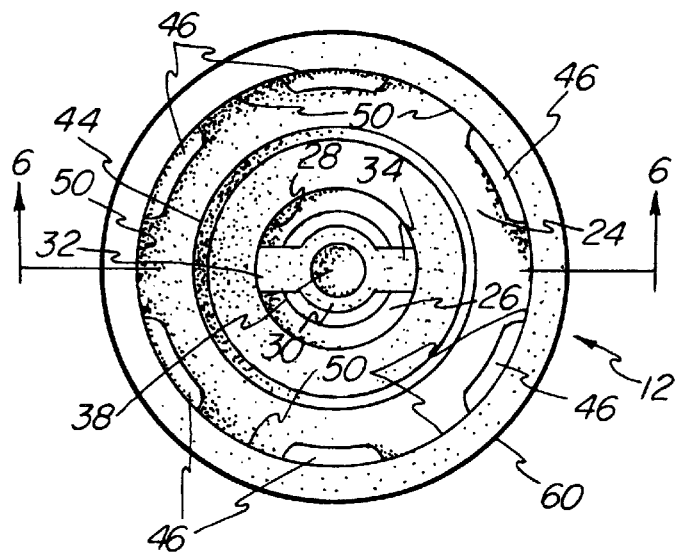
FIG. 5 is an end view of the base member for the valve.
Figure 6:
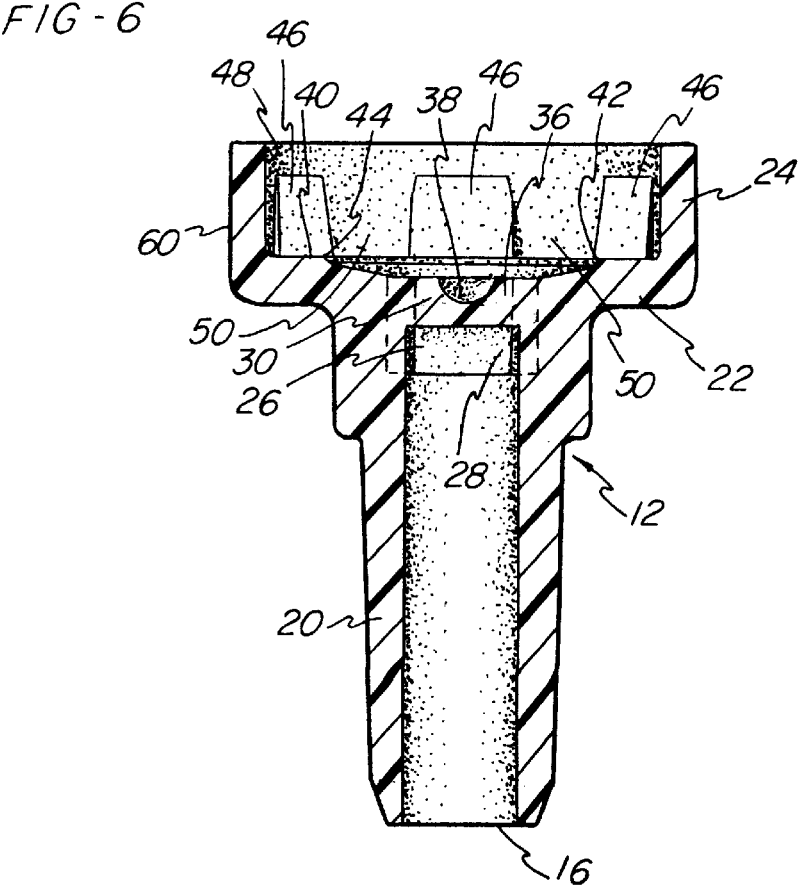
FIG. 6 is an elevational view of a cross section along lines 6—6 in FIG. 5.

Referring to FIGS. 2–4, the outlet 18 of the cap portion 14 is defined by an annular wall 52, and an outlet portion flange 54 extends radially outwardly from the wall 52. A second annular lip 56 extends axially from an outer edge of the outlet portion flange 54 and includes an inner surface 58 engaging an outer surface 60 of the first annular lip 24 in telescoping sealing engagement to thereby define the housing for the check valve 10. In particular, a weld joint 61 is formed between the inner surface 58 and outer surface 60 to form a seal between the base portion 12 and cap portion 14.

The cap portion 14 includes a second inner circumferential wall 62 defining a downstream chamber 64 located adjacent the fluid outlet 18 wherein the downstream chamber 64 defines a cross sectional area which is greater than the cross sectional area of the fluid outlet 18.

A second valve support 66 is supported in spaced relation to the second circumferential wall 62 by a pair of second rib members 68, 69 extending radially inwardly from the second circumferential wall 62. The second valve support 66 extends axially from the downstream chamber 64 through a valve chamber 65 defined by inlet portion flange 22, outlet portion flange 54 and first annular lip 24 and includes an end surface 70 facing toward the upstream chamber 26 and located adjacent to the first valve support 30. The end surface 70 includes a rounded or circular recess 72 formed therein, and the first and second valve support recesses 38 and 72 define a generally spherical space therebetween for receiving the valve element 20.

Referring to FIGS. 1–3 and 7, the valve member 20 comprises a disc shaped element formed of a resilient elastomeric material and defining opposing first and second substantially planar sides 74 and 76, respectively. The valve member 20 defines an axis 78 passing through the geometrical center of the valve member 20 perpendicular to a plane extending parallel to the first and second sides 74, 76. The first side 74 includes a rounded hemispherical portion 80, and the second side 76 is formed symmetrical with the first side 74 and includes a rounded hemispherical protrusion 82 wherein the hemispherical protrusions 80, 82 define a spherical portion located centrally and intersected by the central axis 78.

The protrusion 80 of the valve member 20 is located within the recess 38 of the first valve support 30, and the second protrusion 82 is located within the second recess 72 of the second valve support 66. When the protrusions 80, 82 are captured between the first and second valve supports 30, 66 the first side 74 of the valve member 20 is positioned in normal engagement with the radiused edge 44 of the stepped portion 42 whereby the peripheral portion of the valve member 20 surrounding the protrusions 80, 82 is biased toward the outlet 18 in a concave configuration to define a normally closed condition for the check valve 10.

It should be noted that when the cap portion 14 is brought into association with the base portion 12, a gap 84 typically remains between the annular outer end of the lip 24 and the adjacent surface of the outer portion flange 54, which is the weld depth. The weld depth may be adjusted during assembly to adjust the opening pressure for the valve 10 as a result of adjusting or varying the position of the second value support 66 relative to the first valve support 30. Specifically, to form the valve with a lower opening pressure, the weld depth is increased, and to form the valve with a higher opening pressure, the weld depth is decreased. It may further be noted that the weld joint 61 is preferably formed by an ultrasonic welder that controls the weld depth by sensing of the set travel, rather than being set by hard stops, and that the interference between the base portion 12 and the cap portion 14 is sufficient to permit formation of a shear weld joint while being minimized to permit precise lengthwise adjustment between the base portion 12 and cap portion 14.

When a greater fluid pressure is applied to the valve member 20 through the inlet 16 than the pressure applied to the outlet 18, the outer peripheral portion of the valve member is caused to move out of engagement with the edge 44 to permit fluid flow from the inlet 16 to the outlet 18. In addition, it should be noted that the outwardly angled design of the tabs 46 around the wall 48 provide for a progressively increasing flow area as the peripheral portion of the valve member 20 moves toward the fluid outlet 18. Also, the gaps 50 between the tabs 46 further provide for increased fluid flow past the edge of the valve member 20.

It should be noted that the present design for the check valve 10 provides for ease of assembly whereby the valve 10 may be easily accommodated in an automated assembly process. Specifically, during assembly, a valve member 20 is typically placed in position within the base portion 12 by dropping it down toward the first valve support 30 and, since the valve member 20 is formed as a symmetrical element, it may be oriented with either the first side 74 or second side 76 positioned to face the valve seat 40. Thus, control over the orientation of the valve member 20 as it is inserted in the base portion 12 is not required. Also, the tabs 46 of the base portion 12 guide the peripheral edge of the valve member 20 as it moves toward the first valve support 30 whereby the protrusions 80, 82 are centered relative to the recess 72. Finally, with either the protrusion 80 or 82 positioned within the recess 72, and the valve member 20 thereby properly positioned in contact with the valve seat, the cap portion 14 is placed in telescoping engagement with the base portion 12 and the second valve support 66 moves toward the first valve support 30 to capture the spherical portion defined by the protrusions 80, 82 of the valve member 20. Accordingly, the valve member 20 is readily aligned and captured within the valve housing in a simple manner requiring a minimum of alignment and assembly steps.

The valve 10 provided by the present invention is formed and assembled such that a small biasing force biases the valve member 20 into engagement with the engaging edge 44 in normal sealing contact which, in combination with the structure ensuring precise centering of the valve member 20, results in a valve having very low backflow leakage. In addition, the valve member 20 is clamped in position by the valve supports 30, 66, such that the valve member 20 is held in position in any orientation of the valve to provide reliable operation.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A check valve allowing fluid flow in a first direction and preventing fluid flow in a second direction comprising:

a housing having a first portion defining an inlet and a second portion defining an outlet;

an elastomeric valve member extending diametrically across said housing between said inlet and said outlet, said valve member including opposing first and second sides and a peripheral outer edge;

said valve member defining a geometrically central axis extending perpendicular to said first and second sides;

first and second protrusions extending from said first and second sides, respectively, of said valve member, said first and second protrusions defining first and second engagement surfaces intersected by said central axis;

a first valve support supported on said first portion adjacent said fluid inlet and engaging said first engagement surface in surface contact;

a second valve support supported on said second portion adjacent said fluid outlet and engaging said second engagement surface in surface contact;

a valve seat located on said first portion adjacent said inlet wherein said first side of said valve member engages said valve seat radially outwardly from said first and second valve supports; and wherein said valve member flexes to cause said peripheral outer edge to move toward said outlet and permit fluid flow in said first direction, and said valve member cooperates with said valve seat to prevent fluid flow in said second direction.

2. The check valve of claim 1 wherein said first side of said valve member is symmetrical to said second side of said valve member whereby said valve member is positionable within said housing with either said first side or said second side in engagement with said valve seat.

3. The check valve of claim 1 wherein said first and second engagement surfaces are defined by rounded protrusions and said first and second valve supports include rounded recesses for receiving said first and second protrusions, respectively.

4. The check valve of claim 1 wherein said valve seat includes a step and a radiused portion defined by said step and said step defining an annular sealing edge, and said valve member engaging said sealing edge to prevent fluid flow in said second direction.

5. The check valve of claim 1 wherein said valve member is disc-shaped and said first and second sides comprise substantially planar surfaces extending from said first and second valve supports to said peripheral edge.

6. The check valve of claim 1 wherein said first portion includes an axially extending tip defining an annular outer end, said second portion includes a radially extending flange portion in facing relation to said annular outer end, and a gap is defined between said radially extending flange portion and said annular outer end said gap being proportional to an opening pressure required to move said peripheral outer edge of said valve member off of said valve seat.

7. A check valve allowing fluid flow in a first direction and preventing fluid flow in a second direction comprising:

a housing including an inlet and an outlet;

a disc-shaped valve member located within said housing between said inlet and said outlet;

first and second valve supports supported on said housing; and said valve member being formed with symmetrical opposing first and second sides, said first and second sides each including a protrusion engaged by said first and second valve supports, respectively.

8. The check valve of claim 7 wherein said protrusions comprise a spherical portion located centrally on said valve member.

9. The check valve of claim 8 wherein said first and second valve supports each include rounded recesses for receiving said protrusions.

10. The check valve of claim 7 wherein said first and second sides of said valve member comprise substantially planar surfaces extending from said protrusions to a peripheral edge of said valve member.

11. The check valve of claim 7 wherein said housing comprises a first portion defining said inlet and supporting said first valve support and a second portion defining said outlet and supporting said second valve support, said first and second portions being joined together to define a valve chamber therebetween containing said valve member.

12. The check valve of claim 11 including first rib members extending radially inwardly on said first portion and supporting said first valve support, and second rib members extending radially inwardly on said second portion and supporting said second valve support.

13. The check valve of claim 7 wherein said housing defines a valve seat for engaging one of said first and second sides of said valve member.

14. A check valve allowing fluid flow in a first direction and preventing fluid flow in a second direction comprising:

a housing including a first portion and a second portion;

said first portion including an annular wall defining a fluid inlet, an inlet portion flange extending radially outwardly from said wall of said first portion, and a first annular lip extending axially from an outer edge of said inlet portion flange;

said second portion including an annular wall defining a fluid outlet, an outlet portion flange extending radially outwardly from said wall of said second portion, and a second annular lip extending axially from an outer edge of said outlet portion flange and including an inner surface engaging an outer surface of said first annular lip;

said first portion including a first inner circumferential wall forming an upstream chamber adjacent said fluid inlet and defining a cross-sectional area greater than a cross-sectional area of said fluid inlet, and a valve seat defined on said inlet portion flange and extending radially outwardly from said upstream chamber;

first rib members extending radially inwardly from said first inner circumferential wall;

a first valve support supported by first said rib members in spaced relation to said first inner circumferential wall, said first valve support including a surface facing away said fluid inlet and having a circular recess formed in said surface;

said valve seat including a stepped portion located intermediate said upstream chamber and said first annular lip;

said first annular lip including an inner wall defining a valve chamber and a plurality of protruding, circumferentially spaced tabs on said inner wall which angle radially outwardly in direction from said fluid inlet;

said second portion including a second inner circumferential wall forming a downstream chamber adjacent said fluid outlet and defining a cross-sectional area greater than a cross-sectional area of said fluid outlet;

second rib members extending radially inwardly from said second inner circumferential wall;

a second valve support supported by said second rib members in spaced relation to said second circumferential wall and extending from said downstream chamber through said valve chamber, said second valve support including an end surface facing toward said upstream chamber and having a circular recess formed in said end surface;

a disc-shaped elastomeric valve member having opposed, substantially planar first and second surfaces and a centrally located spherical portion engaged within said recesses in said first and second valve supports wherein said first surface of said valve member is normally engaged with said stepped portion of said valve seat such that said valve seat biases an outer portion of said valve member toward said fluid outlet and said second surface of said valve member is concave;

said valve member being forced into engagement with said valve seat when a fluid pressure is applied to said valve member through said fluid outlet which is greater than a fluid pressure applied to said valve member through said fluid inlet, such that a seal preventing fluid flow is formed between said valve member and said valve seat; and said outer portion of said valve member being moved toward said fluid outlet and out of engagement with said valve seat when a fluid pressure is applied to said valve member through said fluid inlet which is greater than a pressure applied to said valve member through said fluid outlet, such that fluid is permitted to flow from said fluid inlet to said fluid outlet.

* * * * *